(12) United States Patent
Meisal

(10) Patent No.: US 11,179,041 B2
(45) Date of Patent: Nov. 23, 2021

(54) SENSOR SYSTEM AND METHOD FOR CONTINUOUS AND WIRELESS MONITORING AND ANALYSIS OF TEMPERATURE IN ORGANISMS

(71) Applicant: ONiO AS, Oslo (NO)

(72) Inventor: Kjetil Meisal, Oslo (NO)

(73) Assignee: ONiO AS, Oslo (NO)

( * ) Notice: Subject to any disclaimer, the term of this patent is extended or adjusted under 35 U.S.C. 154(b) by 198 days.

(21) Appl. No.: 16/479,209

(22) PCT Filed: Apr. 4, 2018

(86) PCT No.: PCT/NO2018/050088
§ 371 (c)(1),
(2) Date: Jul. 18, 2019

(87) PCT Pub. No.: WO2018/186748
PCT Pub. Date: Oct. 11, 2018

(65) Prior Publication Data
US 2019/0343397 A1    Nov. 14, 2019

(30) Foreign Application Priority Data

Apr. 4, 2017 (GB) ..................................... 1705425
Apr. 4, 2017 (NO) ..................................... 20170555

(51) Int. Cl.
*A61B 5/00*     (2006.01)
*A61B 5/01*     (2006.01)
(Continued)

(52) U.S. Cl.
CPC .............. *A61B 5/01* (2013.01); *A61B 5/6832* (2013.01); *G01K 7/427* (2013.01); *G01K 13/20* (2021.01)

(58) Field of Classification Search
CPC .. A61B 5/01; A61B 5/6832; A61B 2560/0214
See application file for complete search history.

(56) References Cited

U.S. PATENT DOCUMENTS

2006/0122473 A1* 6/2006 Kill .................... G01K 1/024
                                                                600/300
2015/0369764 A1   12/2015 Soon-Jyh et al.
2016/0181501 A1    6/2016 Guillaume et al.

FOREIGN PATENT DOCUMENTS

EP         3296708 A1     3/2018
WO   WO 2016/185905 A1   11/2016
WO   WO 2018/110927 A1    6/2018

OTHER PUBLICATIONS

Examination Report under Section 18(3) in related UK Application No. GB1705425.5, dated Mar. 26, 2020.
(Continued)

*Primary Examiner* — Eric F Winakur
*Assistant Examiner* — Jasim Ahmad Naeem
(74) *Attorney, Agent, or Firm* — Hershkovitz & Associates, PLLC; Abe Hershkovitz

(57) ABSTRACT

A system and method for continuous readout is provided. The object of the invention is achieved by a contact surface for attaching to a surface of an organism, a sensor in thermal contact with the contact surface, a radiochip operatively connected to the sensor, wherein the radio chip will respond to an induced signal from a reader by reading data from the sensor and transmit said data, and method for operating the sensor wherein the data from the sensor is compensated for environmental effects using comprising a second sensor for detecting at least one property from the group comprising ambient temperature, pressure, flow, level, proximity, displacement, bio, image, gas, chemical, acceleration, orientation, humidity, moisture, impedance, capacitance, force, electric, magnetic and mass, thus forming compensated data.

19 Claims, 8 Drawing Sheets

(51) Int. Cl.
G01K 7/42 (2006.01)
G01K 13/20 (2021.01)

(56) References Cited

OTHER PUBLICATIONS

International Search Report in International Application No. PCT/NO2018/050088, dated Jun. 25, 2018.

* cited by examiner

SENSOR SYSTEM AND METHOD FOR CONTINUOUS AND WIRELESS MONITORING AND ANALYSIS OF TEMPERATURE IN ORGANISMS

BACKGROUND OF THE INVENTION

Field of the Invention

The invention relates to a measurement system in general and more specifically a system and a method for measuring and analysing the core temperature of an organism.

Background Art

State of the art is reflected in tympanic (in ear), oral or rectal measurements, and temporal artery infrared sensing. The problem is that these methods require bulky apparatuses, handling by adults and are not suited for continuous manually unsupervised monitoring. In a professional care setting rectal probes are used for continuous monitoring in e.g. neutropenic patients, where fever can develop quickly and where fever is a critical parameter to monitor sepsis. These rectal probes cause major patient discomfort, wounds and risks for additional infections.

From prior art one should refer to traditional thermometers.

WO 2016/185905 discloses a deep body thermometer having a substrate and a heat-receiving terminal for determining a first and a second heat flow.

US 2015/0369764 discloses a system and a method for temperature sensing of three dimensional integrated circuits.

There is therefore a need for a method and a system to overcome the above mentioned problems.

SUMMARY OF THE INVENTION

Problems to be Solved by the Invention

Therefore, a main object of the present invention is to provide a sensor and method for continuous measurement and analysis of the core temperature of an organism.

Means for Solving the Problems

The object is achieved according to the invention by a sensor for measuring temperature of an organism as defined in the preamble of claim 1, having the features of the characterising portion of claim 1, and a method for operating a sensor as defined in the preamble of claim 12, having the features of the characterising portion of claim 12.

In a first aspect of the invention it is provided a sensor for measuring temperature of an organism comprising
- a first layer (104) in thermal connection with the organism,
- a second layer (122) of an insulating material and placed on top of the first layer (104),
- a first temperature sensor (110) in thermal connection with the first layer (104) via the second layer (122),
- a second temperature sensor (120) thermally insulated from the organism is characterised by the first and second temperature sensor being located above the second layer (122).

When referring to the first, second and third layer on top of each other they are organized in a stacked fashion, where the first layer is closest to the organism. The second layer is layered on to the first layer, where the second layer is farther away from the organism than the first layer. On top of should be understood that the layers are stacked horizontally if the first layer is placed on a horizontal surface. Usually also referred to as a sandwich structure. The layers does not need to have same shape, thickness, area, orientation meaning that the layers may partially overlap while still maintaining the form of a stack of layers.

Preferably the sensor comprises at least one additional sensor s measuring second physical property of the group comprising temperature, pressure, fluid flow, heat flow, level, proximity, displacement, bio impedance, image, light, gas, chemical, acceleration, orientation, humidity, moisture, impedance, capacitance, force, electrical, magnetic, mass and audio. Such would be advantageous of improved monitoring of the organism.

Preferably the sensor (100) is characterised by further comprising a third layer above the second layer, preferably the third and first layer comprise metallic material. One advantage is that layers can operate as capacitive storage of electrical charge.

Preferably the sensor is characterised by further comprising means for harvesting electrical energy (142) and at least one energy storage unit wherein the harvested energy is stored in the energy storage unit. One advantage is that the energy can be stored for later use. The energy can be harvested from the surroundings using means for converting photovoltaic, thermoelectric, piezoelectric, electromagnetic, magnetic, electric, oxidation, electrostatic, bio-energy into electrical energy.

Preferably the sensor is characterised by further comprising processing means for sampling the first and second temperature sensor. One advantage is that the temperature sensor data can be converted to a digital format. The processing means is programmable and alterable, where said processing means can have at least one property from the group comprising alterable mode of operation, sensor operation, store data, process data, encrypt data, decrypt data, interpret data, operate and calibrate auxiliary components and self-destruct. In addition a memory device may be provided to allow storage of sensor data for later retrieval.

Preferably the sensor is characterised in that the energy storage unit is at least one capacitive storage, preferably formed of at least two metallic layers (104,106) and at least one insulating layer (122) of the sensor (100). The energy storage unit can also be a battery, fuel cell or similar.

Preferably the sensor is characterised in that the sensor further comprises a radiating element wherein the first layer is a reflector for the radiating element, wherein an insulating material is creates a distance between the antenna radiating element and the reflector. One advantage is a compact design.

Preferably the sensor is characterised in that the radiating element, the insulating material, and the reflector forms an energy storage unit for storing harvested energy. One advantage is improved size.

Preferably the sensor is characterised in that the reflector comprises a capacitive storage device for storing harvested energy from the energy harvesting means. One advantage would be reduced size of unit and ease of manufacturing of the device.

Preferably the sensor is characterised in that the radiating element functions as receiving element for energy harvesting. One advantage is that energy from radio waves can be harvested.

Preferably the sensor is characterised in that the processing means is coupled to at least one selected from at group comprising the energy harvesting means, energy storage unit, and capacitive storage device for powering the processing means to sample data from at least one sensor (110, 120) and the processing means is coupled to the radiating element for transmission of the at least one sampled sensor data. One advantage is that the unit can be powered from its surroundings, operate for periods without access to harvesting energy as previous energy is stored in the device.

Preferably the sensor is characterised in that the sensor further comprises an indicator coupled to the processing means, preferably a coloured light. The indicator could be a LCD screen, e-ink screen, white light or other device that can provide visual indication to a user of an alarm situation.

In second aspect of the invention it is provided a method for estimating the core temperature of an organism using a sensor according to claim 1 placed on the surface of the organism, wherein the method comprises the steps:
  measuring the temperature from the first temperature sensor,
  measuring the temperature from the second temperature sensor,
  calculating the core temperature according to heat flux calculations using the measurement from the first and the second temperature sensor.

In a third aspect of the present invention it is provided for use of a sensor for measuring the surface temperature of an organism.

A number of non-exhaustive embodiments, variants or alternatives of the invention are defined by the dependent claims.

The term "continuous" is in this context understood to mean a measurement system that repeatedly performs measurements, regardless of user intervention, given that the system is enabled. For monitoring body temperature in humans, this may mean measurements as rarely as 2 times each minute, to accommodate the required sampling rate relative to how fast body temperature can change and the preferable resolution of ±0.1° C. Examples of rapid changes can be caused by malignant fever, remittent fever or similar. Such rapid changes may be less than 1 degree every 10 minutes, and to accommodate Shannon's sampling theorem and detection of temperature changes within ±0.1 degree Celsius, a sampling rate of 2 samples every minute is required.

The present invention attains the above-described object by temperature sensor sharing a contact surface with an organism. The contact surface provides an excellent thermal contact with the organism where the temperature of the organism can be measured. A mixed signal semiconductor allows for the temperature and other physical parameters of the organism to be quantified, signal processed, stored and distributed. Preferably, the distribution is by means of a wireless communication link. The communication link is enabled by a central reader that generates a carrier wave and a modulated transmission. The carrier wave in turn modulated by the mixed signal semiconductor, typically used in backscatter wireless systems, for example RFID.

A sensor system for continuous readout is provided, comprising a contact surface for attaching to a surface of an organism, a sensor in thermal contact with the contact surface, a RFID chip operatively connected to the sensor, wherein the RFID chip will respond to an induced signal from a reader by reading data from the sensor and transmit said data.

Preferably the system is encapsulated in a resilient material while the contact surface is exposed.

Preferably the contact surface is coated with an adhesive layer.

Preferably, the system harvests energy from it surrounding and stores it in a designated storage unit. This is advantageous in batteryless applications.

Preferably, the system is programmed and can be programmed to perform tasks as such as operate sensors, signal processing, algorithm work, data processing, store data and operate the backscatter radio based on a defined program. An example of such program could be to power up its sensor engine, record sensor data, power down sensor engine, and store the sensor data with timestamps 1 time every minute, regardless of reader contact, as long as the power is sufficient.

Preferably, the system can operate independently based on a program and operate sensors and store data such as sensor data for later readout or transmission. This is advantageous in that the system can operate autonomously.

Preferably, the system harvest energy from its surroundings and stores it in a designated energy storage unit.

Preferably, the system is programmable and can be programmed to perform tasks such as operate sensors, compute data, store data and operate the radio based on the defined program.

Preferably, the system can operate independently based on a program and operate sensors and store data for later readouts. Preferably, the system further comprises an antenna located on any side relative to the contact surface using a resilient material, wherein the distance between the antenna and the contact surface provides an antenna gain.

Preferably the system further comprises an antenna, comprising a radiating element located on a side separated from and substantially opposite to a metallic reflector. The radiating element and the metallic reflector is spaced apart by a material, where the dimension of the material defines the space between the radiating element and the reflector and the antenna gain by the electromagnetic properties of such spacing material and the radiating efficiency of the radiating element. This to reduce the absorption effects from the organism e.g. human body, mammal, animal etc. Such reflector can be implemented in such a way that it can double up as energy storage for a system, and as heat transfer element for heat flux to allow lower cost and less complex manufacturing.

Preferably, the metallic layer for the antenna is designed as a multilayer structure, where the layers are separated by an insulator and where the layers are practically implementing a single or multidimensional capacitor, to serve as an energy storage unit.

Preferably, the metallic layer serving as a metallic reflector for the antenna are designed as a multilayer structure, where the layers are separated by an insulator, to serve as a energy storage unit.

Preferably the insulator separating the metallic layers have known and constant thermal conductivity, transferring heat to the upper-most layer of the multi layer reflector structure.

Preferably, the upper layer of said structure is connected by a heat and electrically conducting material to a layer where the sensors are located. Said connection can be a thin pin or VIA connecting one temperature sensor thermally.

Preferably, an insulating material is placed between the multilayer reflector upper layer and the layer where the temperature sensors are connected.

Preferably, an additional temperature sensor is located on the upper layer of this insulator, separating the heat from the contact surface by a known and good insulator.

Preferably, the two temperature sensors are located on the same structural level to be used for performing heat flux measurements, e.g. for estimating core temperature.

Preferably the system further comprises a second sensor for detecting at least one property from a group comprising temperature, pressure, heat flow, fluid flow, level, proximity, displacement, bio, image, impedance, illumination, gas, chemical, acceleration, orientation, humidity, moisture, impedance, capacitance, resistance, force, electrical, magnetic, sound, noise, audio and mass.

Preferably the system further comprises 2 or more of the same sensor, forming a cluster of sensors.

The cluster of sensors can be used together to measure complex value such as flow or combined to compensate for environmental impact such as drift and noise.

Preferably, a combination of sensors for temperature, moisture and bio impedance can be of great value for detecting sweat, dehydration, and fever in one. Enabling care for fever and preventing patients from laying soaking in sweat, and providing advice to levels of hydration necessary for ill patients which can be critical with e.g. elderly patients.

Preferably a combination of one or more temperature sensors and an acceleration sensor is used to detect fever cramps and spasms of the organism.

Preferably a combination with a capacitance sensor can e.g. detect that the sensor has been placed on skin, and e.g. enable touch capability for e.g. on/off functionality. Preferably the system further comprises a positional detector.

In some embodiments a method for operating a sensor is provided, wherein the data from the sensor is compensated for environmental effects using a second sensor for detecting at least one property from a group comprising temperature, pressure, flow, level, proximity, displacement, bio, image, gas, chemical, acceleration, orientation, humidity, moisture, impedance, capacitance, force, electric, magnetic, and mass, thus forming compensated data. Preferably from the group further comprising a combination of e.g. carolis flow sensor, and two accelerometers a low cost blood flow and pressure sensor can be implemented providing low cost, comfortable, non invasive mean for continuous monitoring for home use for e.g. patients being subscribed with beta blockers.

Preferably, and alarm is raised when the data from the sensor is outside a predefined range, e.g. when the fever rise above 39.5° C.

Preferably an alarm is raised when the compensated data from the sensor is outside a predefined range, e.g. when ambient temperature is above 35° C.

Preferably, an alarm is raised when the data from the second sensor is outside a predefined range, e.g. when temperature is above 45° C.

Preferably, an alarm is raised when the combined data from two or more sensors are outside a predefined range, e.g. when fever is high in combination with high ambient temperature. E.g. fever of 40° C. in combination with ambient temperature above 35° C.

A sensor system and method for continuous and wireless monitoring and analysis of temperature in organisms, such system comprises of a wireless sensor system integrated preferably as a flexible adhesive bandage, which is placed on the surface or skin of an organism. Preferably, the system is provided with means for energy harvesting from its surroundings and means for storing the harvested energy in a energy storage unit. Such energy harvesting can be implemented as rectification a carrier wave used in wireless communication or rectification of terrestrial broadcast signals such as radio or TV bands. The harvested energy is stored in the energy storage unit such as capacitor, rechargeable battery or similar storage unit for storing electrical energy for later use. An alternative system is capable of boosting the small electrical potential from a photovoltaic cell or a more traditional fuel cell. The capacitor ca be as previously mentioned be realized by means of the two metal bodies (layers) already used for temperature flux measurements A wireless reader capable of reading sensor data using a defined radio protocol, or several protocols in combination, in addition to e.g. sensing ambient conditions, and transmitting such data to an eco-system which can be implemented as a e.g. network cloud solution, and said eco-system with methods and signal processing for presenting simplified quantifiable data to an end user device and enabling individual adjustable notifications based on such data, access to history of data as well as a big data access platform to such ecosystem, with methods for analysis which can be used for location, tracking and new insight in information on temperature in organisms and trends, one of these uses can be monitoring increased temperature usually referenced to as fever in an organism, e.g. in a human having, caused by e.g. infections. Combining user provided information on the organism, and its geolocation, which e.g. can be derived from the user device, for additional analyses can have one example of tracking geo located data and infection patterns through such ecosystem. One example can be tracking infections in humans, and spread of infection in the society using geolocation and the characteristics of the febrile response over time, which can map to known fever patterns and known infections. Such use would be of great value to health care authorities and medical research and can contribute greatly to the knowledge on registered and unregistered illness in the society with respect to; infection source tracking, infection spread tracking and generally increased knowledge on registered and unregistered illness causing febrile responses. As an example, such device can be used in both developed and undeveloped parts of the world to improve knowledge, countermeasures and aid in both epidemic and non-epidemic outbreaks.

Effects of the Invention

The technical differences over prior art is that it is possible to wear the sensor system continuously without discomfort and the sensor has a higher degree of integration and precision of measurement. Other technical differences are the sensor is provided with means for energy harvesting and storage of energy. The reflective layer in the sensor also effectively shields the radiating element from the electrical absorption in the skin creating an improved antenna system.

These effects provide in turn several further advantageous effects:
- it makes it possible to monitor an organism continuously, such as humans and animals,
- it makes it possible to use the measurement system continuously and without supervision by a caretaker or patient,
- it allows for valid reading of sensor also in the presence of varying ambient temperature, moisture and even when covered,
- it allows for continuous measurements, even if the reader or power source is out of range,
- it allows for a wireless and passive sensor integration at low cost, which enable consumable fever sensors limiting infection risks with reuse, it allows for fewer patterns to be used as an indication to identify infectious and non-infectious diseases in organisms, it allows for anomalies in body temperature, like increased frequency or amplitude of normal variations to be detected, as an early warning of sepsis developing in e.g. neutropenic patients, it allows for temperature alerts on e.g. high and low temperatures and without supervision, it allows for a low cost sensor enabling widespread use in professional and domestic health care settings, it allows for non-invasive monitoring of organisms, it allows for a more comfortable monitoring of patients and organisms, e.g. critically ill patients, it allows for a simple visual feedback from the reader or the sensor to signal alarm/no-alarm condition, it allows for reduced reliance on one-time use power sources as battery, it allows for an easy to use monitoring system, it allows for a more efficient system to monitor organisms, and it allows for a smaller system for monitoring of organisms.

BRIEF DESCRIPTION OF THE DRAWINGS

The above and further features of the invention are set forth with particularity in the appended claims and together with advantages thereof will become clearer from consideration of the following detailed description of an [exemplary] embodiment of the invention given with reference to the accompanying drawings.

The invention will be further described below in connection with exemplary embodiments which are schematically shown in the drawings, wherein.

DESCRIPTION OF THE REFERENCE SIGNS

Figure 1:
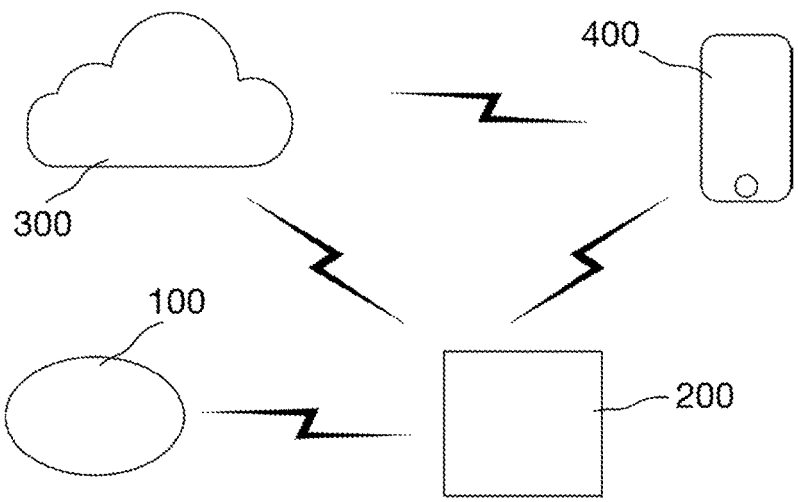
FIG. 1 shows a system comprising sensor implementation, reader, ecosystem and user device.
Figure 2:
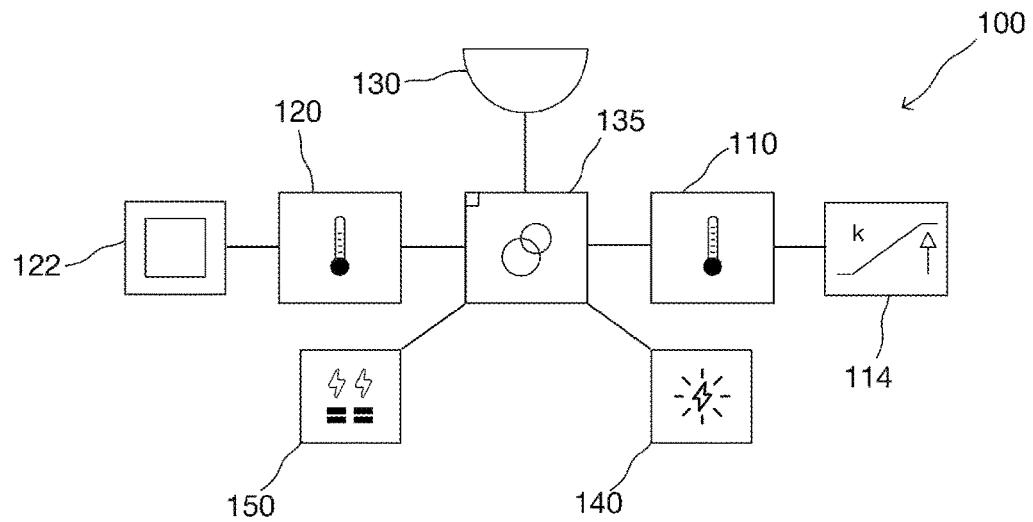
FIG. 2 shows the sensor implementation with antenna, radio chip, sensors, energy harvesting, thermal conductor, thermal insulator and energy storage.
Figure 3:
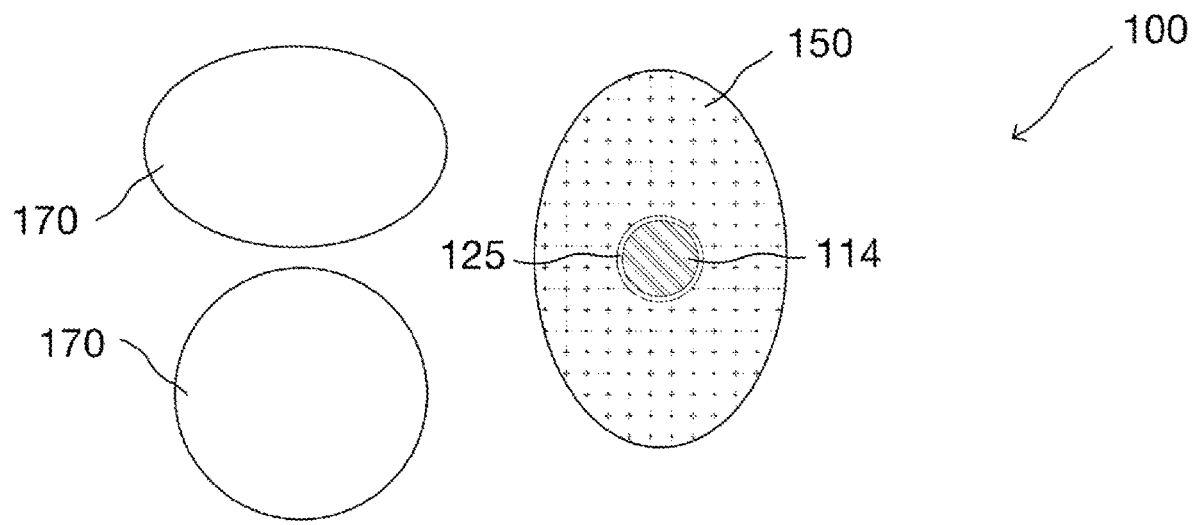
FIG. 3 shows the sensor implementation and examples of shapes and the space between thermal conductor and adhesive.

The following reference numbers and signs refer to the drawings:

100 The sensor implementation with the antenna, radio chip, sensors and thermal conductor
101 Bonding wire
102 Bonding wire connected to RF rectifier
103 Copper (CU) top layer heat conductor to ambient
104 Exposed metal connected to contact surface
105 PCB Via operating as a heat pipe/conductor
106 Metal layer
107 PCB VIA operating as an electrical connection only, not heat pipe/conductor
110 Temperature sensor connected to radio chip
114 Thermal conductor
120 Temperature sensor connected to the radio chip
122 The thermal insulator, substrate
124 Heat flux between the two thermistors
125 The space/gap between the thermal conductor and the metal backing and adhesive under the antenna part of the sensor implementation
130 The antenna part of the sensor implementation
132 The dedicated antenna area of top layer
133 The transition and connection to a thermistor on the bottom layer
135 The radio, protocol and controller part of the sensor implementation
137 The cut out in the antenna area in the design, where the connection to the second sensor are routed
138 The metallic reflector part of the antenna
139 The cut out in the metallic reflector to fit the connection to the thermal conductor
140 The energy harvesting part of the sensor implementation
142 The dedicated energy harvesting area of the top layer
144 The print layer of the sensor implementation
150 Energy storage part of the sensor implementation
152 The adhesive fixing the sensor implementation to the measured surface
155 The cut out in the adhesive, where the thermal conductor connection to the skin is located
170 The sensor implementation and some examples of shape variations
180 The main substrate where the sensors chips and antenna are embedded
182 The connection wiring between two sensors
200 The reader with antennas, radio reader chip, processing chip, interfaces, data storage, sensors and airflow design -continued 210 The radio reader chip
220 The radio reader antenna
230 The processing and interface chip
240 The data storage in the reader
250 The readers wired interfaces
260 The antennas for the reader wireless interfaces
270 The ambient sensors in the reader
280 The airflow design for the reader ambient sensors
290 The radio for wireless interfaces
300 The ecosystem with interfaces, signal processing algorithms, processing and storage systems
310 The ecosystems user storage
320 The ecosystems sensor data storage
330 The ecosystems product database
340 The ecosystem interface for Big data access
350 The ecosystem interface for end user access
360 The ecosystem processing unit
370 The ecosystem signal processing algorithms
400 The end user device
420 The end user device with application or web browser, and its storage unit
422 The end user device with application or web browser
424 The storage unit in the end user device
500 The Temperature heat flux measurement setup
510 Tissue/skin heat transfer coefficient
515 Heat Flux between core and tissue/skin
520 Core Temperature $T_C$
610 Air in measurement environment
615 Heat flux between sensor 100 and environment

DETAILED DESCRIPTION OF THE INVENTION

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The invention will be further described in connection with exemplary embodiments which are schematically shown in the drawings.

For the apparatus presented in FIG. 1 being an e.g. fever or temperature monitoring system intended for home use and especially children, the alternatives that exist and are mostly used today are Tympanic (in ear), oral or rectal measurements, and temporal artery infrared sensing. By children most of these are considered uncomfortable e.g. in ear, oral or rectal measurements, and they are not continuous. The most comfortable approach existing is the temporal artery infrared sensing approach, however this does not allow continuous measurements. A few Bluetooth based devices allowing continuous measurements has emerged, however these comprise batteries and some electronics, which will make the total cost of ownership for a consumer to high for widespread use. The fact that these devices are based on Bluetooth, makes them less user friendly, as it limits the user device to be within range of the sensor, which can be a challenge in environments with building materials like reinforced concrete. It also limits the number of sensors that a user can observer continuously. This results in that the user and the user device needing to stay in the same room as the sensor in order for the user device to get continuous data from the sensor and alarms. Backscatter radio technology, is best known in the form of RFID, which has existed for years and are in most approaches designed for electronic identification in large logistics operations and security applications in some form, where you have a reader infrastructure reading large volumes of tags.

Principles Forming the Basis of the Invention

The underlying principle is that a wearable sensor can be used for continuous monitoring by integrating a sensor with backscatter radio and antenna into a low cost sensor system without batteries, in a packaging with an adhesive for attachment to a surface of an organism. A reader utilizing the same backscatter radio technology induces power to the sensor system and reads the available data from the sensor. In use the sensor can be repeatable read by a reader and thus allows for practical low cost and continuous use, enabling a broad area of use and more substantial amount of sensor data from areas where continuous data on a big scale has never been available. The system comprises one or more temperature sensors that are easy to manufacture using easy accessible manufacturing processes, such as traditional printed circuit boards. The preferred temperature sensor comprises an arrangement of two thermistors. Closest to the surface of the organism is a metal layer with one thermistor thermally connected to it. The there is a layer of a material with known and preferably constant thermal coefficient. As a third layer is a second metal layer with a second thermistor thermally connected to the third layer. By measuring the thermistor values with a suitable analogue to digital converter, the heat flux can be deduced and a suitable algorithm can be applied to calculate the core temperature. The metal layer in the first and third layer can have arbitrary shape, preferably the metal layer in the first and third layer have corresponding shape. Preferably, the two metal layers have as much as possible overlap. Instead of having to use cumbersome techniques where the first thermistor is buried in between the first and the third layer a novel use of PCT vias is applied. The via are used as a heat pipe so that both thermistors can be on the same PCB level. The temperature sensor is particularly compact in size, easy to manufacture, and low cost using few components.

BEST MODES OF CARRYING OUT THE INVENTION

The embodiment of the apparatus according to the invention shown in FIG. 1 comprises a flexible sensor implementation 100, a radio reader 200 that reads sensor data and stores it in an ecosystem 300 comprising data processing and presentation formatting, and presents the data to a user through a user device 400, which can be an application on a cellular phone. Such system described can be a temperature sensor implementation 100, where the system is designed to measure surface temperature on the forehead of a human being, for instance a child, and calculate the core temperature of the human using the ecosystem and present this in a continuous manner to e.g. parents or alternative caretakers, and serve as an apparatus for continuous fever monitoring to provide continuous information on the development, trend, and severity of such fever development. When a medical physician is contacted due to an illness causing a febrile response, such data can be presented and analysed to aid the medical physician in a diagnosis process. Such a system would be available to a consumer through e.g. online stores, pharmacies, or a local supermarket, where the consumer would expect to find fever monitoring equipment. Available product bundles could be a reader together with several sensors, and bundles of several sensors with e.g. different print on. Such an apparatus would not only improve fever monitoring and care for sick children, bringing peace of mind to both the child and parent. It could also be a new unexplored area for research on illness causing febrile response, as such scale of data on febrile development does not exist today. Most available continuous fever data today are from monitoring on sick patients in a hospital. Monitoring spread of illness in the society could have a great socioeconomic value, through reducing or preventing large outbreaks in an early stage.

The system presented in FIG. 1 is designed for continuous, wireless monitoring and analysis of temperature in organisms, e.g. humans and animals. This system comprises of a flexible sensor implementation 100 e.g. like an adhesive bandage, shaped in any way, e.g. circular, square, rectangle or oval, that can harvest energy from its surroundings, sense the temperature and wirelessly transmit it. The harvesting of energy can be induced radio waves, received solar energy, thermic energy converted to electrical energy via peltier elements where temperature difference between skin and air is used to generate electrical energy, electrical energy converted from movement via e.g. pietzo electrical devices. A reader 200 that can wirelessly transfer energy to the sensor system and receive the transmission from the sensor implementation 100, add ambient sensor information like e.g. temperature and humidity from internal sensor 270, and send this to an ecosystem 300, which can be implemented in e.g. a network cloud solution. This ecosystem implementation will have methods for storing and for quantifying data and send data to the end user, preferably in real-time. The end user will interface the system through a device 400, e.g. through an application on a device like a smartphone or a web interface through any computer. The reader 200 can also as a backup solution when there is no connection to the ecosystem, transfer the data directly to the device using a wireless technology like e.g. Bluetooth, where an example can be the application on the user's device, which also have methods for quantifying the data in real time and presenting it to the user, receives and processes the data. In the backup scenario, the data is stored in the data storage unit of the device for later syncing with the ecosystem. If the reader during shorter periods loses connection with the ecosystem or device in backup mode, it has the means through internal storage to store data until connection with the ecosystem or device in backup mode is working again.

Figure 4:
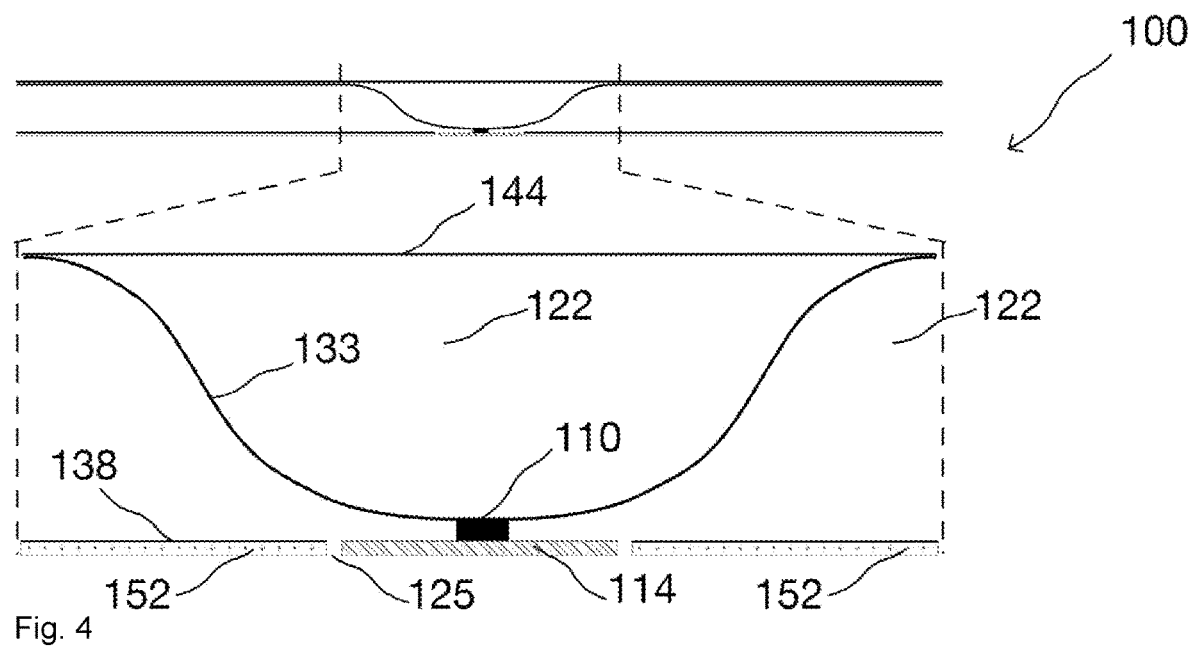
FIG. 4 shows the thermal conducting layer connected to the sensor, and the connection to the antennas and insulating layer surrounding the sensor.
Figure 5:
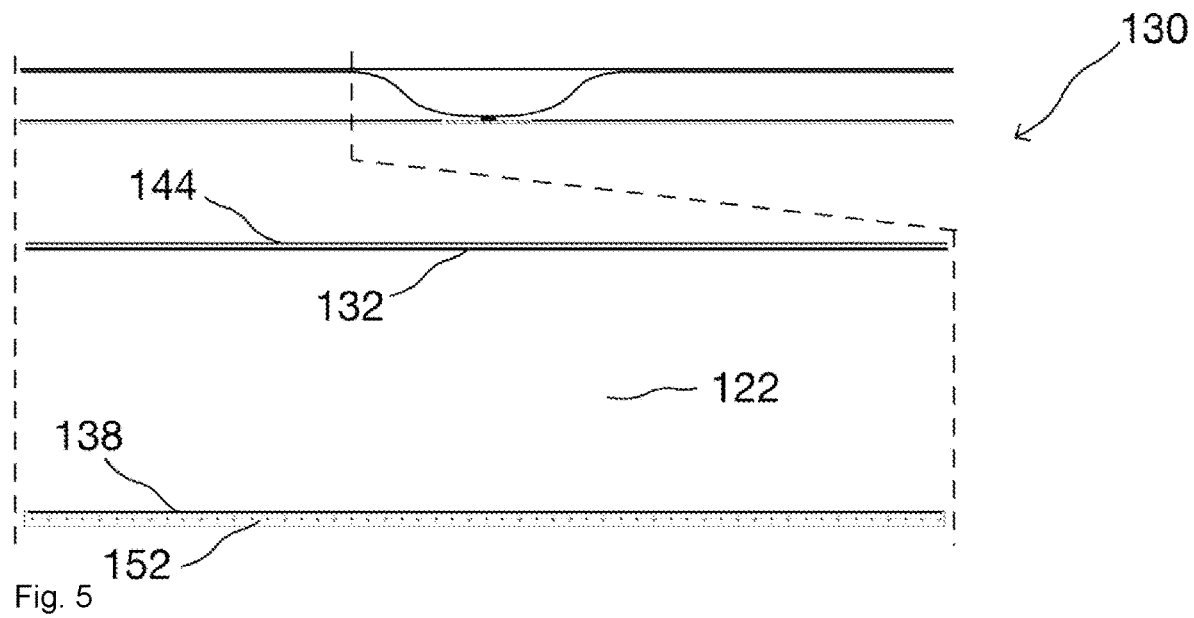
FIG. 5 shows the antenna part of the sensor implementation, with the spacing material and metal reflector.

The sensor implementation 100 is the key to the system and is built as a multi-layer structure to combine properties of long range backscatter communication and optimized temperature sensing conditions. This can be achieved in several ways, where a first approach can be e.g. a single sensor approach as illustrated in FIGS. 4 and 5, and a second approach can be a dual sensor implementation using temperature heat flux measurement 500 as illustrated in FIGS. 2, 6, 7, 12, 13, 14, 15, 16 and 17. The sensor implementation 100 shown in FIG. 2 comprises an antenna 130, a radio chip 135 which could comprise both an integrated temperature sensing functionality, and an radio and protocol part, including a possible interface to e.g. power and communication with external sensors 110, 120, which can be a temperature sensor. A thermal conductive layer 114, a thermally insulating layer 122, and a print layer 144. The sensor implementation may also comprise an energy harvesting unit 140 that can harvest energy from the surroundings.

The antenna 130 is designed in such a way that it is minimally affected by the absorption of the radiated energy caused by the properties of e.g. the skin and human body. Such feature is obtained by designing the antenna 130 in a way that limits such absorption of energy. Approaches to cope with this can be one or a combination of the following; separating the antenna radiating element 132 from the skin by a given distance using spacing material 122, applying spacing material with a selected electromagnetic properties, changing the resonant frequency of the antenna, applying a metal reflector 138 between the antenna and the skin, or other approaches known by the skilled in the art. The antenna 130 will hence be designed in such a way that it is either immune to the material that it is place, or that it constructively uses the features of the material that it is placed onto to improve its radiating performance.

Figure 6:
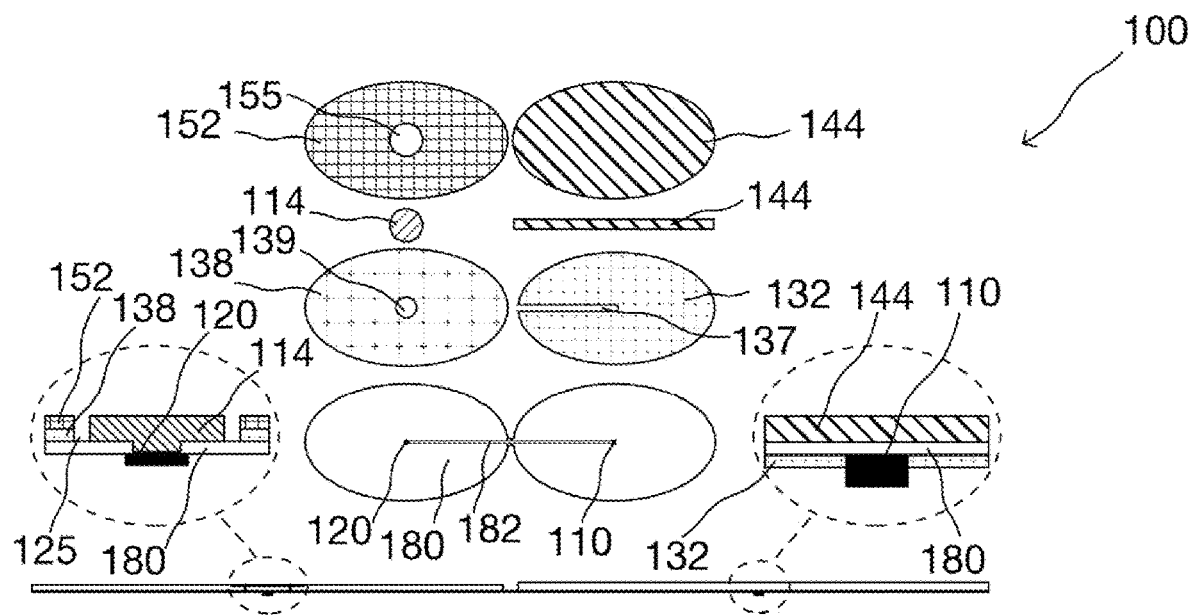
FIG. 6 shows the sensor implementation build-up and parts for heat flux mode measurement.

FIG. 6 shows the thermally conductive layer 114 in the sensor implementation enables direct and good thermal contact with the surface, e.g. human skin the sensor implementation 100 is placed on. The thermal conductor 114 can be placed in a cut out area 155 of the adhesive layer 152 and cut out area 137 of the metallic reflector 138, with a space/gap 125 which can be designed in between the thermally conductive layer 114 and the lower metallic layer/metallic reflector 138 of the antenna design 130 in order to avoid a good thermal connection and electrical connection between the thermal conductor 114 and metallic reflector 138, avoiding lateral heat loss or heat transfer to 138, and reducing ESD challenges for the radio chip 135 and external sensor 110 and 120. The thermally conductive layer 114 will be in direct contact with the measured medium, and the radio chip 135 with the integrated sensor and external sensor 110 in single sensor mode, and the external sensor 120 in heat flux temperature sensing mode, is thermally connected to thermally conductive layer 114 using a thermally conductive glue or similar compound both fixing the radio chip 135 and external sensor 110 and 120 as well as being a good thermal conductor. Both the radio chip 135 and sensors 110 and 120 will be in DIE form or other packaging with good thermal conductivity. The thermal connection to the sensor 120 could be made through e.g. a perforated area in e.g. a PET substrate, which could be filled with the thermally conductive glue used to fix the thermal conductor 114 to the sensor 120.

Figure 7:
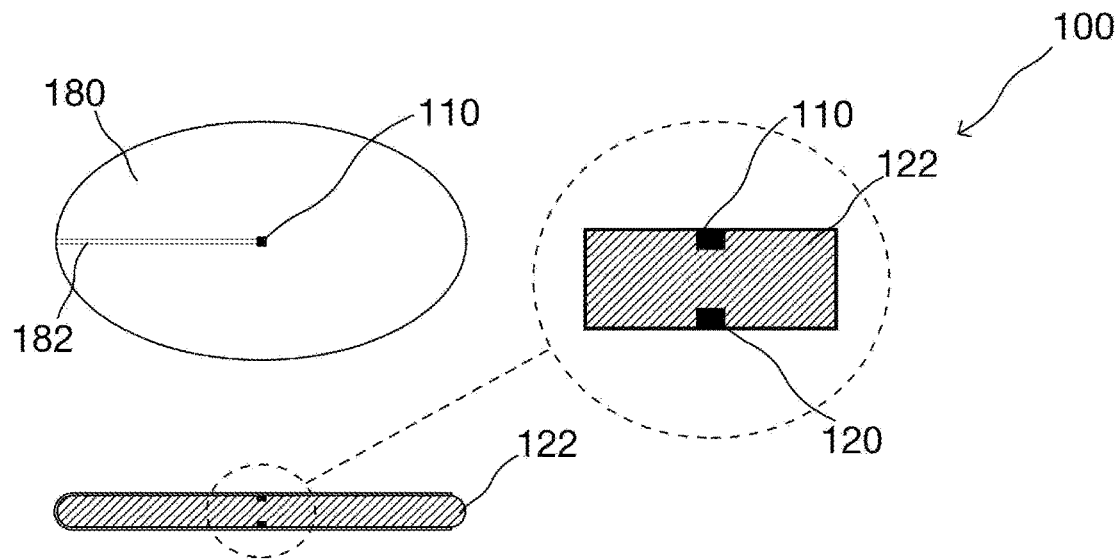
FIG. 7 shows the basic folding of substrate with radio chip and external sensor mounted around the insulator material for heat flux mode measurements.

The transition 133 from the antenna radiating element 132 on the top layer of the sensor implementation to the connection of the radio chip 135 in the single sensor approach as shown in FIG. 5, or the folding of the substrate around 122 illustrated in FIGS. 6 and 7, enables the combination of two features; good range performance in an antenna placed on conducting or absorbing surfaces, and good thermal contact between the internal sensor and the sensors 110 and 120 and the measured medium. Referring to FIGS. 4 and 5. The transition 133 from the antenna radiating element 132 to the lower layer of the sensor implementation in the single sensor approach is optimally shaped as e.g. a planar cut of a sphere, as an arc where the radio chip 135 is located at the centre bottom of this shape. The bottom centre of the shape is located at one of the lowest layer in the sensor implementation 100, while the antenna radiating element 132 connected to the outer edge of this shape is located at the second layer from the top, directly under the print layer 144. The substrate comprising the antenna radiating element 132 and the shaped transition 133 and the connected radio chip 135 is one piece, assembled on e.g. a flexible PET substrate or similar, and shaped during production. The radio chip 135 is typically glued to the substrate, using an electrically conductive glue, or other suitable material or method that allows for maintaining electrical connection while the substrate is bent.

The area between the bottom of the shaped transition 133 and the top layer is filled with an insulating material 122 in order to reduce the effect from ambient temperature, and loss of heat from the measured surface. Such insulating material 122 can be e.g. closed cell polyethylene foam or similar materials. In addition, the reflective layer in the antenna structure 138, can be of e.g. metallized BoPET (Biaxially-oriented polyethylene terephthalate) or similar insulating material in order to reduce the loss of heat from the measured surface. Both insulating techniques in combination with the thermal conductor 114 will help reduce the time for temperature equilibrium for the internal temperature sensor and the sensors 110 or 120. This is achieved as the insulator 122 will reduce the thermal conductivity between the sensor 110 and the ambient conditions, The metal sheet insulator 138 in the antenna 130 will reduce the thermal conductivity for the whole surface area covered by the sensor implementation 100, while the thermal conductor 114 will increase the thermal conductivity to the surface of the medium being measured.

Now referring to FIG. 6. In the heat flux sensor approach, the substrate 180, which can be e.g. a flexible PET substrate, can be assembled as one piece in production, similar to the single sensor approach, but with the external temperature sensor 120 located away from the radio chip 135. An approach for the substrate in the heat flux sensing approach, can be to produce it two times the size of the sensor implementation 100, connect the external sensor 110 using connection wires 182 routed through a cut out or keep out area of the antenna area 139, and with a feature to fold it around a material 122, which serves as the antenna spacer between the metallic reflector 138 and the antenna radiating element 132, and as an insulator reducing heat loss from the surface, features known electromagnetic properties and a known heat transfer coefficient, the material can e.g. be optimized for a more compact antenna design 130, or as a good insulator. Both the thermal conductor 114 and the insulating material 122, both in the single sensing and heat flux sensing approach, will have known thermal properties, and the sensor data from 110 and 120 in combination with the ambient sensor data from the reader 200, an algorithm and signal processing system 370 can estimate the organisms true core temperature from its surface temperature, applying known compensation techniques from literature, e.g. medical literature for human core temperature estimation. Changes in ambient conditions can be detected by the ambient sensors 270 in the reader 200, before it effect the sensor 110 or 120, and as the effects from ambient to the sensor 110 or 120 in the sensor implementation 100 is known, this effect can be compensated for in the signal processing algorithm system 370.

Figure 9:
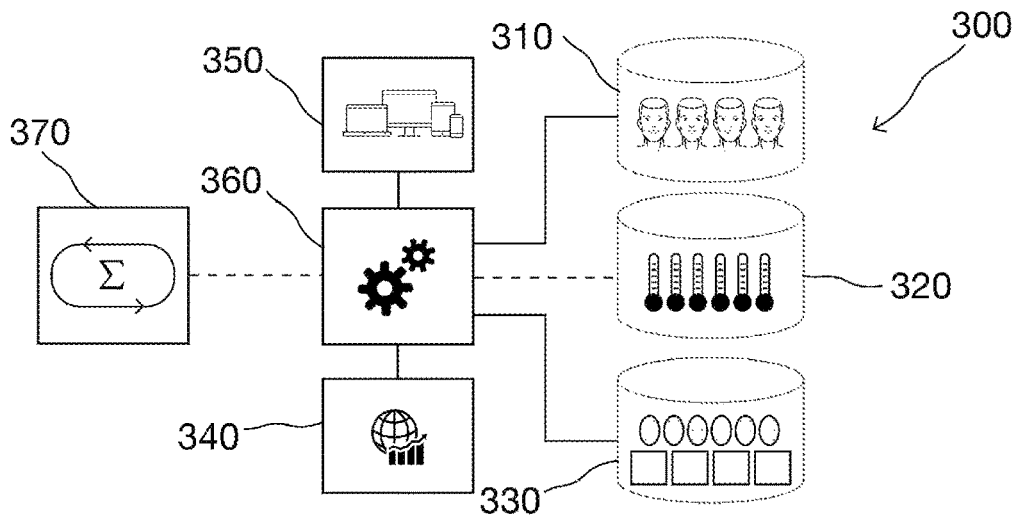
FIG. 9 show essential parts of the ecosystem with interfaces, signal processing algorithms, processing and the different storage systems.

The single sensor signal processing algorithm system 370, shown in FIG. 9, measures the surface temperature of the organism, e.g. the skin temperature of a human, and uses known compensation techniques like wet/dry bulb compensation techniques for moisture e.g. a constantly defined difference between surface and core temperature, combined a temperature leakage compensation to ambient conditions using sensor information from the sensor 270 in the reader 200. The heat flux sensing approach utilizes two sensors 110 and 120 and calculates the core temperature 520 by calculating the heat flux from the core through the tissue and skin 515, using the difference between the two sensors readings and the known heat transfer coefficient 124 of the material 122 in between to calculate the heat flux through the material 122. The following equation can be a central part of such calculation when used to e.g. calculate the core temperature of humans, shown in FIG. 17:

$$T_C = T_A + \frac{h_A}{h_B} * (T_A - T_B) \quad \text{Equation 1}$$

Where:
$T_C$: The core temperature
TA: The temperature of sensor A 106
TB: The temperature of sensor B 114
$\phi_{qCA}$: Heat flux between core and skin 515
$\phi_{qAB}$: Heat flux between sensor A 106 and sensor B 114
$h_A$: Heat transfer coefficient 510 of the tissue/skin
$h_B$: Heat transfer coefficient 123 of the insulating material 122

The reason for the sensor implementation 100 structure: Utilizing known data on heat transfer coefficient of the organism e.g. human body's skin/tissue, an optimized and known thermal conductivity between the skin and the sensor 110 and 120 and 110 in single sensor mode, a known heat transfer coefficient 124 of the insulating material 122 and a known thermal conductivity to the ambient conditions in the sensing environment, an algorithm can be applied to predict the organisms core temperature with high accuracy. The combination of antenna design, shapes to connect the radio chip in the single sensor approach, and folding in the heat flux approach, thermal connection to the sensor, and insulation to the ambient conditions maintains an optimal combination of antenna and sensor performance for long range continuous and passive RFID sensor applications of surface temperature and core temperature estimation in organisms.

The lower layer: The bottom layer located on the same layer as the thermal connection to the measured medium (e.g. skin), will be an adhesive layer 152 with e.g. hypoallergenic properties that does not cause any harm to the organism it is applied on.

The top layer: The top layer will be a printable layer for artwork. This layer will be a thin layer of a material causing no effect to the antenna performance, like thin paper.

Figure 8:
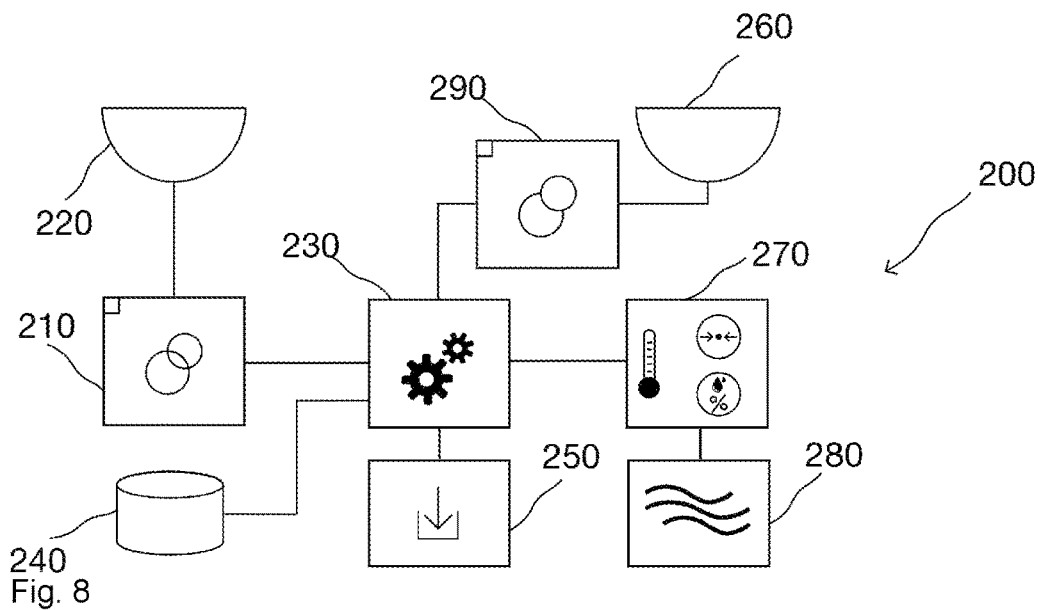
FIG. 8 shows the reader and its antennas, radio chip, processing chip, sensors, interfaces, storage and airflow design.

The Reader 200 (shown in FIG. 8) is designed as a portal to the ecosystem for the radio sensor implementation 100. The design can comprise a radio reader chip 210, a processing unit 230, internal storage 240, internal sensors 270, wired interfaces 250, radio for wireless network interfaces 290, antenna for wireless network interfaces 260, and radio antenna 220 and if the sensor 270 is an air quality and/or temperature sensor, an air flow design for the sensor 280. The reader 200 reads the sensor implementation through a custom read plan, where e.g. radio chips 135 in sensor implementations require, a certain amount of induced energy, which can be ms to accumulate enough power to perform sensing using the internal sensor 110 and/or external sensors 120 and/or others and communicate e.g. the appropriate sensor information, calibration data, ID and other information to the reader 200. Further the reader 200 and read plan is customized in such a way that it is optimized for low power consumption, duty cycling communication to the sensor implementation 100 and hence its measurement frequency, and the communication interval to the ecosystem 300, allowing the reader system to sleep cyclically. Through this implementation a sensor can be read several times sequentially, and oversampling can be applied to increase resolution and reduce noise in temperature measurements, which change slowly compared to the applied read rate, hence increasing temperature measurement accuracy of the sensors, which following can increase the accuracy of the core temperature calculation. The standard wireless and wired network communication protocols and methods implemented in the reader 200 can work as a single main channel for communication to the ecosystem 300, and e.g. comprise backup systems in case the main communication fails. Further the reader 200 can comprise backup storage to use in case main communication channel fails temporarily, and/or the backup communication channel fails temporarily. The reader 200 may also comprise methods in e.g. hardware or software for encryption of data being communicated to the ecosystem. Through the network connections to the reader 200 e.g. through IP addresses, it can record the current geolocation to the ecosystem for purposes which can be e.g. setting the mode of operation due to regulatory requirements, location and tracking epidemic and non-epidemic illnesses in the society, looking up local environment conditions which can be temperature, humidity and barometric pressure. Further the reader design comprises an air flow design 280, separating the ambient sensors 270 from effects caused by e.g. heating of air inside of reader 200 or dry air inside of reader 200, ensuring a more correct sensing of ambient conditions.

The ecosystem 300 (as shown in FIG. 9) can be designed to e.g. store data on products 330, sensor readings 320 and users 310, as well as comprise signal processing algorithm methods 370, with an implemented algorithm e.g. as described in Equation 1 and a processing unit 360, running the signal processing algorithm methods 370, on the sensor data, using the e.g. equation 1 to calculate the core temperature of the e.g. human being. Further the ecosystem 300 can comprise different interfaces for the user side 350 and big data side 340. Such ecosystem 300 can be implemented as e.g. a network cloud solution or on any other device or unit. The ecosystem 300 can be designed to store the unique ID of all products designed and produced to be a part of the ecosystem 300, which can be e.g. sensor implementations, readers and other devices, limiting counterfeit products to compromise the e.g. user experience and/or quality and usability of the sensor data. In such ecosystem 300 the interface for users 350 could easily limit individual users' access to data, to be the data generated by the user's products only. And the interface for big data could easily limit the data not to comprise user identifiable data, which can be e.g. e-mail addresses, names, notes, images and similar. Further the ecosystem could by storing all unique product IDs in a database, limit operation time of products, to ensure the quality of readings is not compromised by e.g. sensors being used over a long period and e.g. causing faulty data due to reduced thermal connection with the surface of the organism.

The thermoregulation is an organism is part of a homeostatic mechanism that strives to maintain optimal operating temperature. The temperature is not a constant as it varies during the day, over days and over populations of individuals. In humans the average of such temperature is 37.0° C., however due to the normal rhythms in temperature, the normal temperature is defined as a range: 37.0±0.5° C. A rise in normal temperature can be caused by sever factors, and are divided into two main definitions, fever and hyperthermia. Fever is a condition where the organism's temperature is raised above the normal range, this is known as febrile response or pyrexia. Fever caused by a raised setpoint in the thermoregulation, which mostly happen due to both infectious and non-infectious medical conditions. Hyperthermia on the other hand is caused by a situation where the organism is producing more heat than it can dispose of, which can be caused by ambient conditions with high temperatures (heat stroke), or adverse reactions to drug use. In this situation the setpoint is not raised. Temperatures higher than 37.2° C. in the morning or higher than 37.7° C. in the afternoon are normally considered as fever. The ranges of fever temperatures are classified as: fever >37.5° C., Hyperthermia >37.5° C., and Hyperpyrexia >40.0° C. Hyperpyrexia can be life-threatening and is considered a medical emergency. Fever (or temperature) development over time reveals a certain pattern of fever (fever pattern). These patterns have been known and used to aid diagnosing illness since the antiquity, and are usually classified as: Continuous fever, intermittent fever, Remittent fever, Pel-Ebstein fever, Undulant fever and Relapsing fever.

Figure 10:
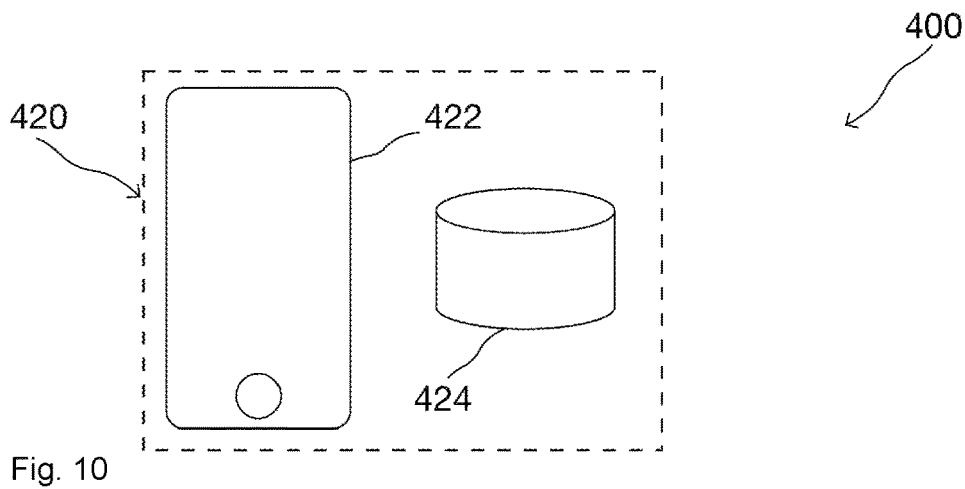
FIG. 10 shows the user device in the system, and the storage unit of such device.
Figure 11:
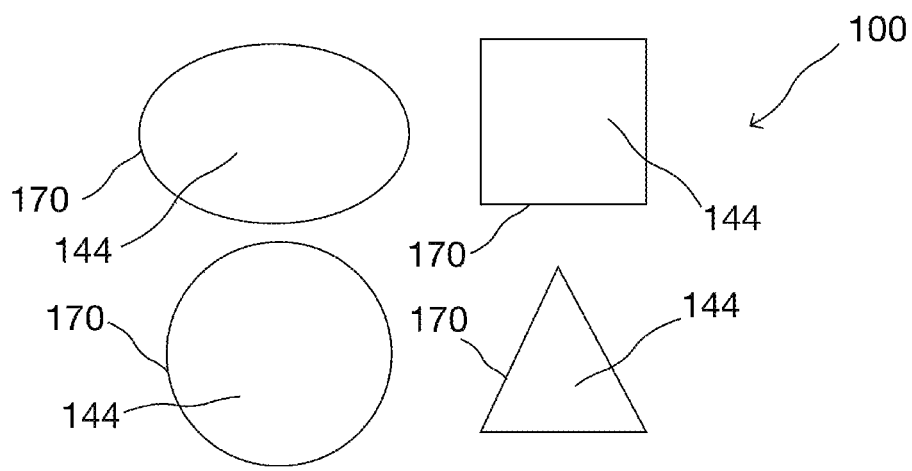
FIG. 11 shows the sensor implementation and examples of shapes.

The end user device 400 (as shown in FIG. 10) comprises an interface designed as an e.g. web interface, application on a smart device or other. This interface 422 can e.g. present real time data from an ongoing measurement, and set and adjust notifications based on the change of this data over time. Such notifications can be e.g. high fever alerts, or a given level of fever over a long period for humans with a condition causing a febrile reaction. Alerts based on other sensors, like an accelerometer, where a fever seizure alarm can be triggered by the body movements during seizure. History of data e.g. short term or long term and former individual measurements could be accessed through the interface 422. The end user device 420 could comprise a storage unit 424, which could be used to e.g. temporarily store data in case a back up communication solution to the reader is active, and/or there is no connection to the ecosystem 300 or data history or external storage. Further the user interface 422 could comprise an fever reducing drug administration as well as general state of health registration feature, which could comprise a timestamp and which could be a simple graphical button in a graphical user interface, and which could support registration of the actual drug including amount and brand, which could be implemented as a software correlating camera input from e.g. a smart device used to scan a optically readable product code on such drug packaging and correlate such information to public drug databases. Such information on fever reducing drug administration could then be used in e.g. correlation with the sensor data to explain e.g. unexpected changes over time and the amount of drug administration in addition to the general state of health to a e.g. a medical doctor when analyzing human fever data. Further the end user device 400 could comprise a radio reader chip to induce power to and read data from the sensor implementation 100 directly. This could be performed using e.g. NFC, RFID etc.

Figure 12:
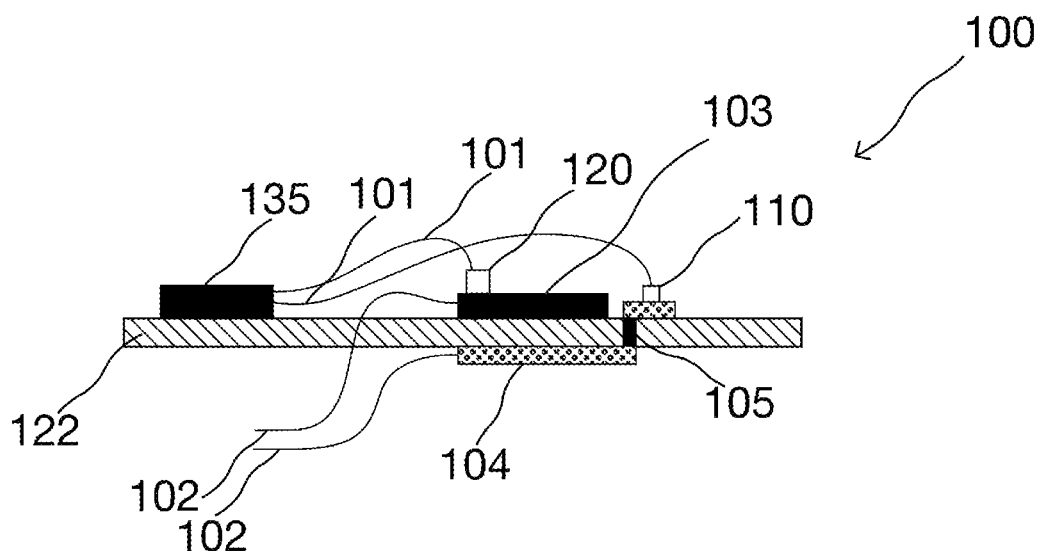
FIG. 12 shows the sensor implementation with radio chip, heat flux sensor build using two thermistors, thermally conductive and thermally insulating materials.
Figure 13:
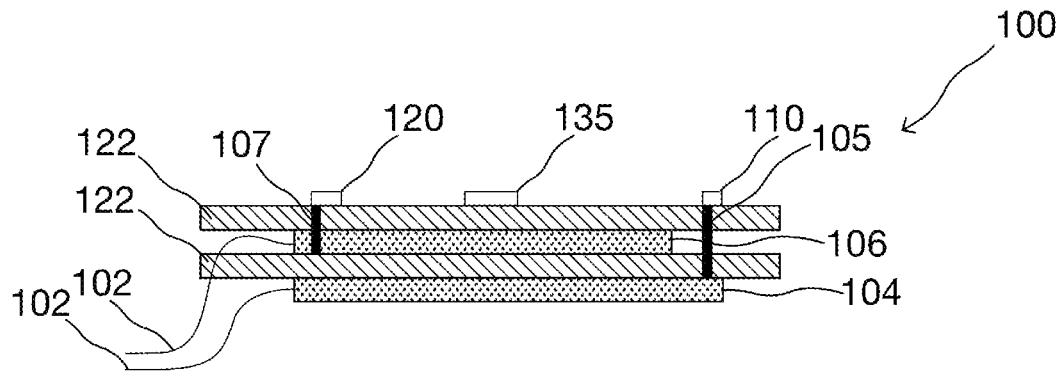
FIG. 13 shows the sensor implementation with radio chip a heat flux sensor build using a multi layer structured material, like standard PCB providing the thermally conductive and thermally insulating materials.
Figure 14:
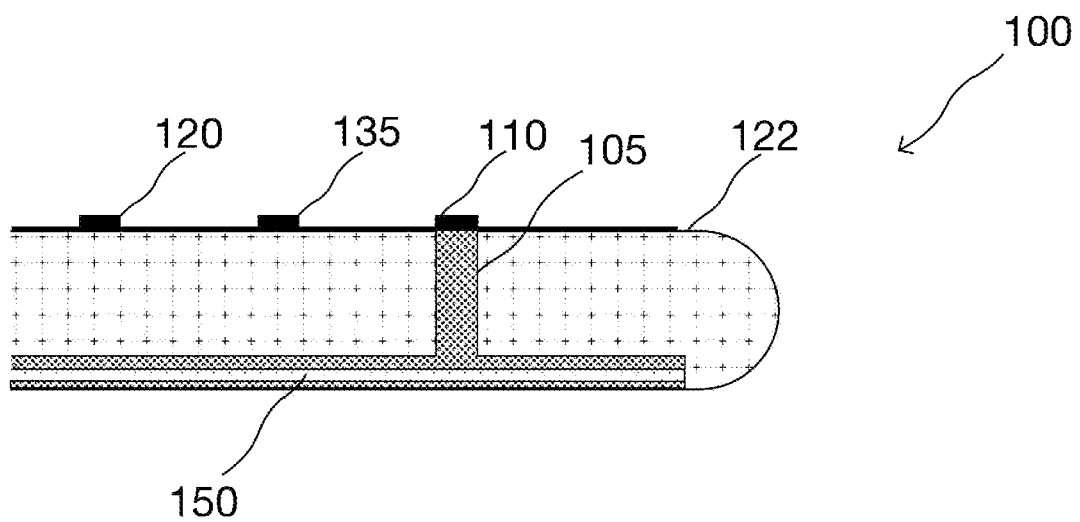
FIG. 14 shows the sensor implementation with radio chip and a heat flux sensor build using two thermistors, where the components are assembled on a flexible substrate which is folded around a thermally insulating material with an additional functionality as an energy storage device.
Figure 15:
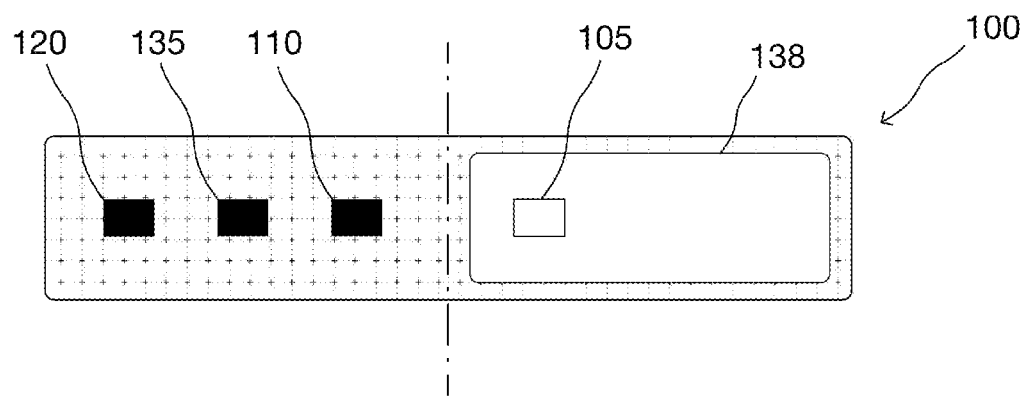
FIG. 15 shows the sensor implementation with radio chip and heat flux sensor build using two thermistors, where the components are assembled on a flexible substrate, showing the heat pipe connecting the contact surface to one of the thermistors.

In FIG. 13 a second embodiment of a sensor implementation is shown. The sensor implementation 100 is built as a multi-layer structure to combine properties of long range backscatter communication and optimized temperature sensing conditions, incorporating energy storage in the multi layer structure and energy harvesting from the environment. The sensor implementation 100 comprises an antenna 130, a radio chip 135 which could comprise both an integrated power harvesting unit 140, and temperature sensing functionality using two thermistors 110 and 120, and a radio and protocol part, including a possible interface to e.g. power and communication with external sensors, which can be temperature sensors. A Thermal conductive layer 104, a thermally insulating layer 122, and a print layer 144. The sensor implementation may also comprise an external energy harvesting unit 140, comprising one or more means for harvesting energy from its surroundings. An area on the antenna layer 142 (see FIG. 16) can be dedicated to energy harvesting, allowing implementation of e.g. energy harvesting antenna structures and solar panels, harvesting electromagnetic and light energy. In FIG. 12, 13, 14 various embodiments of the sensor stack up is shown. The sensor build for heat flux sensing is built with a thermally conductive layer 104, in contact with the contact surface, and with a temperature sensor 110, connected thermally with a piece of good thermal conductor 105, like metal, going through the thermal insulator 122. The piece of thermal conductor 105 and on the top of the insulator material, hence they are located on the same layer, enabling the second temperature sensor 120 to be located on top of the insulator 122, thus temperature sensor 110 and 122 represent a heat flux measurement while being located on the same layer, allowing less complex and lower cost production. Further the thermally conductive layer 104 double up as a part of the antenna, serving as a reflector, reducing energy absorption from the human skin. Said layer can be implemented as a multi layer metal structure, where the metal layers are implemented as thin sheets, separated by thin sheets of an isolator material with good thermally conducting properties. Said multi layer structure 104,106 hence also serves as a energy storage device and are connected to the energy harvesting engine 140.

FIG. 12 shows the thermally conductive layer 104 in the sensor implementation 100 enables direct and good thermal contact with the surface, e.g. human skin the sensor implementation 100 is placed on. The thermally conductive layer 104 will be in direct contact with the measured medium, and the sensor 110 through a heat pipe 105 implementation, while sensor 120 is located on top of the thermal insulator 122 forming a heat flux sensor.

Figure 16:
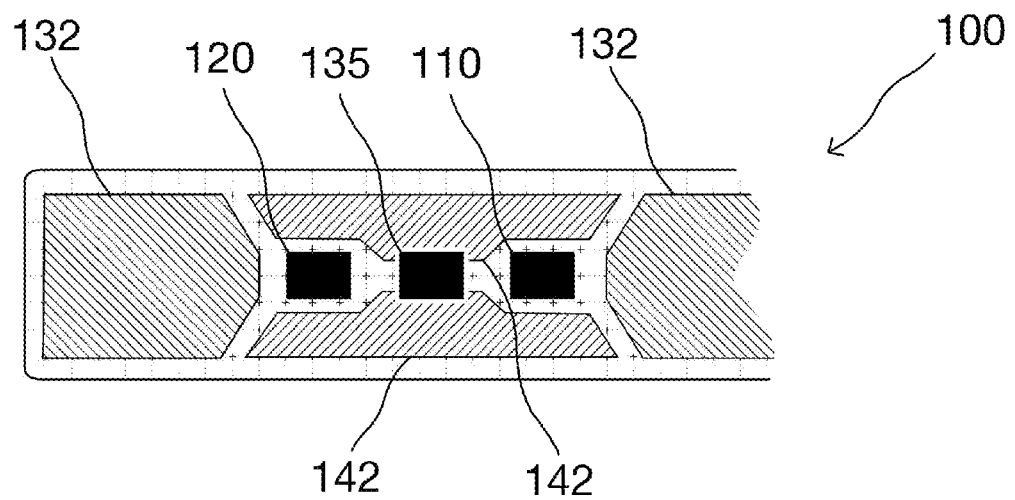
FIG. 16 shows the radio chip and the two thermistors on the layer together with the areas dedicated for communication antennas and energy harvesting.
Figure 17:
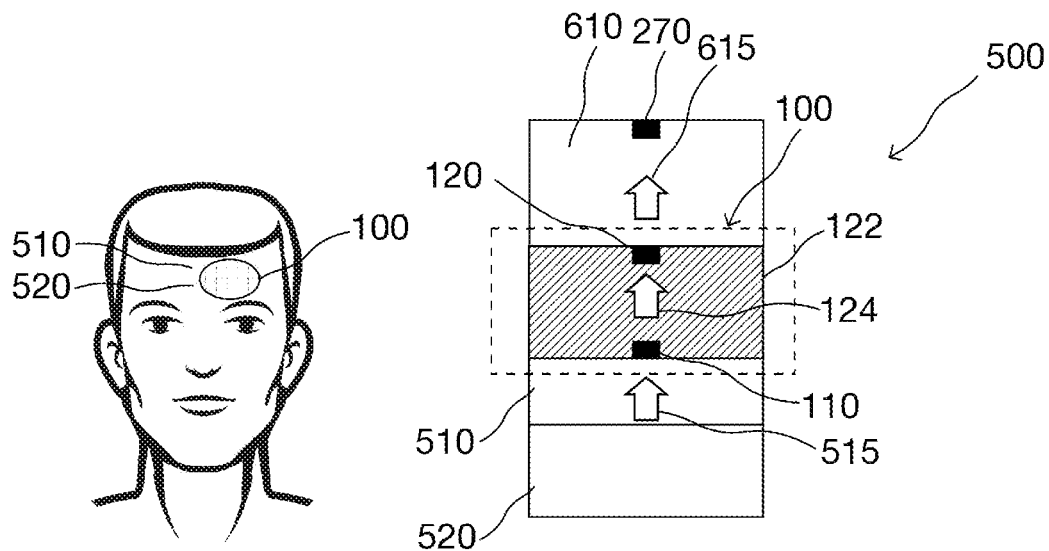
FIG. 17 shows concepts and parts for Heat flux mode temperature measurement and reference to core temperature. Including the heat flux channel to ambient.

In FIG. 16 the substrate comprising the antenna radiating element 130, power harvesting element 142, temperature sensors 110 and 120 and radio chip 135 can be designed as one piece, assembled on e.g. a flexible PET substrate or similar, and shaped during production. Enabling low cost roll to roll production. The components are typically glued to the substrate, using an electrically conductive glue, wire-bonding or other suitable material or method that allows for maintaining electrical connection while the substrate is bent.

Insulating material used in contraction with said flexible substrate can be e.g. closed cell polyethylene foam or similar materials.

In FIG. 7 a second heat flux sensor approach is shown, the substrate 122, which can be e.g. a flexible PET substrate, can be assembled as one piece in production. Both the thermal conductor 104 and the insulating material 122 in heat flux sensing will have known and constant thermal properties, and the sensor data from 110 and 120 in combination with the ambient sensor data from the reader 200, an algorithm and signal processing system 370 can estimate the organisms true core temperature from the heat flux sensor data. Changes in ambient conditions like e.g. temperature, humidity and barometric pressure can be detected by the ambient sensors 270 in the reader 200, before it affect the heat flux sensor, and as the effects from ambient to the heat flux sensor in the sensor implementation 100 is known, this effect can be compensated for in the signal processing algorithm system 370.

The heat flux sensing approach utilizes two sensors 110 and 120 and calculates the core temperature 520 by calculating the heat flux from the core through the tissue and skin 510, using the difference between the two sensors readings and the known heat transfer coefficient of the material 122 in between to calculate the heat flux through the material 122. The following equation can be a central part of such calculation when used to e.g. calculate the core temperature of humans, shown in FIG. 17. The calculations are using the equation 1 mentioned earlier.

The reason for the sensor implementation 100 structure: Utilizing known data on heat transfer coefficient of the organism e.g. human body's skin/tissue, an optimized and known thermal conductivity between the skin and the sensor 110 and 120, a known heat transfer coefficient of the insulating material 122 and a known thermal conductivity to the ambient conditions in the sensing environment, an algorithm can be applied to predict the organisms core temperature with high accuracy. The combination of sensor implementation in a compact multilayer structure, utilizing antenna reflector and antenna radiating structure as energy storage devices, and utilizing the antenna reflector as a heat transfer design, allow the Heat flux approach to be implemented in a compact low cost form factor. Combining the antenna design for backscatter radio with energy harvesting, energy storage features and the sensor build maintains an optimal combination of antenna and sensor performance for long range continuous and passive backscatter radio sensor applications of core temperature estimation in organisms.

The lower layer: The bottom layer located on the same layer as the thermal connection to the measured medium, will be an adhesive layer 152, e.g. a Silicone Gel Adhesive with hypoallergenic properties that does not cause any harm to the organism it is applied on, as well as being waterproof and resistant to bacteria. The adhesive is preferably thin and thermally conducting with known thermal conductive properties.

The top layer of the sensor implementation: The top layer will be a printable layer for artwork. This layer will be a thin layer of a material causing no effect to the antenna performance, like thin paper.

Figure 18:
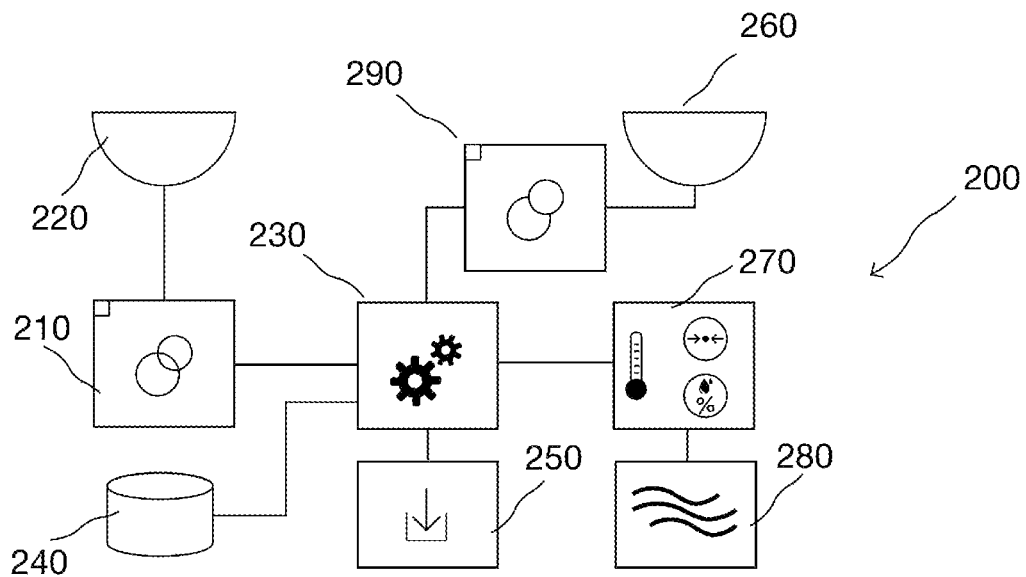
FIG. 18 shows the reader and its antennas, radio chip, processing chip, sensors, interfaces, storage and airflow design.

FIG. 18 shows a second embodiment of The Reader 200 is designed as a portal to the ecosystem for the radio sensor implementation 100. The design can comprise a radio reader chip 210, a processing unit 230, internal storage 240, internal sensors 270, wired interfaces 250, radio for wireless network interfaces 290, antenna for wireless network interfaces 260, and radio reader antenna 220 and if the sensor 270 is an air quality and/or temperature sensor, an air flow design for the sensor 280. The reader 200 reads the sensor implementation through a custom read plan, where e.g. radio chips 135 in sensor implementations require several time units of induced signals which can be ms to accumulate enough power to perform sensing using the sensors 110 and 120 and communicate e.g. the appropriate sensor information, calibration data, ID and other information to the reader 200. Further the reader 200 and read plan is customized in such a way that it is optimized for low power consumption, duty cycling communication to the sensor implementation 100 and hence its measurement frequency, and the communication interval to the ecosystem 300, allowing the reader system to sleep cyclically. Through this implementation a sensor can be read several times sequentially, and oversampling can be applied to increase resolution and reduce noise in temperature measurements, which change slowly compared to the applied read rate, hence increasing temperature measurement accuracy of the sensors, which following can increase the accuracy of the core temperature calculation. The standard wireless and wired network communication protocols and methods implemented in the reader 200 can work as a single main channel for communication to the ecosystem 300, and e.g. comprise backup systems in case the main communication fails. Further the reader 200 can comprise backup storage to use in case main communication channel fails temporarily, and/or the backup communication channel fails temporarily. The reader 200 may also comprise methods in e.g. hardware or software for encryption of data being communicated to the ecosystem. Through the network connections to the reader 200 e.g. through IP addresses, it can record the current geolocation to the ecosystem for purposes which can be e.g. setting the mode of operation due to regulatory requirements, location and tracking epidemic and non-epidemic illnesses in the society, looking up local environment conditions which can be temperature, humidity and barometric pressure. Further the reader design comprises an air flow design 280, separating the ambient sensors 270 from effects caused by e.g. heating of air or dry air inside of reader 200, ensuring a more correct sensing of ambient conditions.

Figure 19:
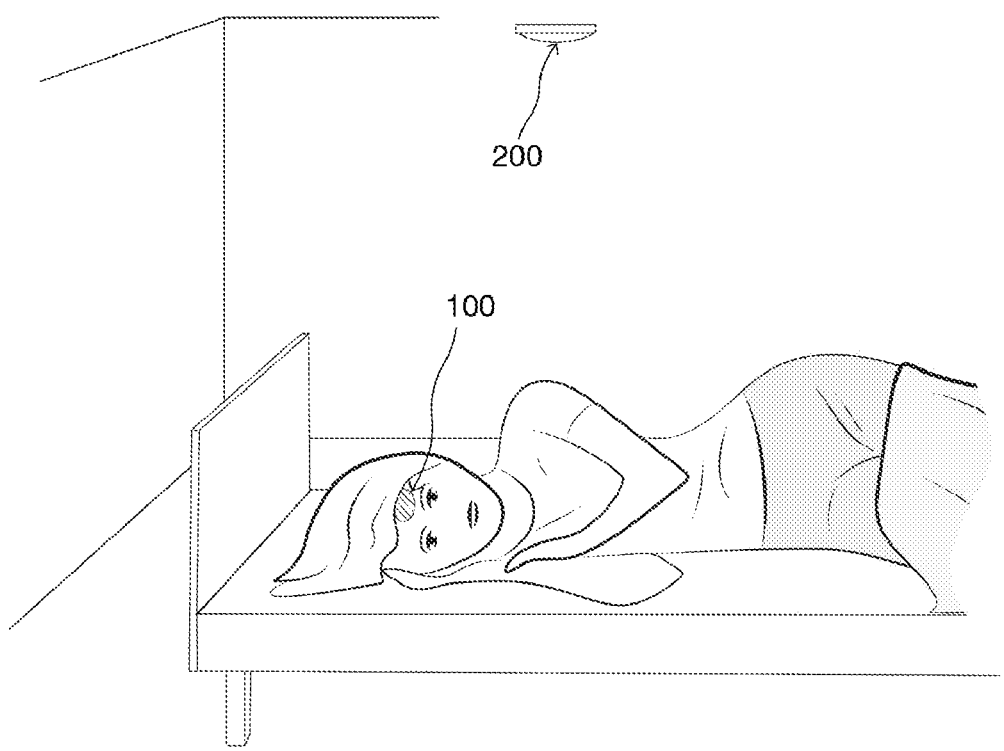
FIG. 19 shows a typical user scenario with a reader in ceiling and sensor on user forehead.

FIG. 19 shows a typical scenario where a reader 200 is located in the ceiling and a sensor 100 is attached to the forehead of a patient.

Alternative Embodiments

A number of variations on the above can be envisaged. For instance using an antenna 130 in the wireless sensor implementation, where the antenna is designed by those skilled in the art to operate on the surface of the organism e.g. human skin, and not in air.

Another variation is to design the antenna 130 in such a way that it uses the organism or parts of the organism constructively e.g. like the frontal skull bone in a human cranial, to improve antenna performance.

Another variation can be implementing the wireless sensor system in a different substrate material and shape, designed to be used on in different ways on an organism. For a human this can be e.g. a contact lens or an earplug, earring or other jewelry, or implemented in shoes, clothing fabric, bandages, medical casts or plaster, briefs, diapers, sanitary pads, pantyliners, prosthesis, corsets or other medical and non medical support or aid devices.

Another variation of this could be a wireless sensor implementation using multiple radio protocols and standards, allowing a wider range of use and operating ranges. This can e.g. be multiple radio protocols, a combination between existing and new radio protocols, custom protocols based on the latter, or multiple other radio protocols.

In some embodiments of the sensor in use for elderly patients a combination of a temperature sensor, moisture and a chemical sensor like a PH sensor, implemented in e.g. a brief, would provide means for higher quality of living for the elderly and better quality assurance for routines in a e.g. elderly care home. A sensor combination like this would be able to classify content of the brief in addition to detect early indications on several medical and non medical conditions like; acidosis, dehydration, diarrhea, starvation, kidney failure and urinary tract infection.

In other embodiments a combination of temperature, pressure, proximity, orientation, displacement and acceleration implemented as a sensor system could e.g. detect the use of medical support aids, if located in between the skin and a e.g. corset used post surgery on many back and neck injuries and post correcting surgery from birth defects. This system would then be able to detect amount of use, if used correctly e.g. too tight or too loose, patient movement and activity during use, and support aid displacement during use. Giving a medical doctor a data foundation to support and aid further patient advice, treatment and motivation for improved results.

In yet other embodiments a combination of sensors combining temperature, moisture and light, e.g. ultraviolet light, could serve as a sensor system detecting hyperthermia/overheating and overexposure to sunlight for children and elderly. In some embodiments one or more temperature sensors can be combined with a bio impedance sensor, the system can then also detect dehydration.

In yet other embodiments the sensor is combined with one or more sensors from the group comprising temperature sensing, moisture and PH levels in combination with bio impedance could serve as smart bandages for e.g. burns, detecting if the wound needs attention due to; increased surface temperature relative to core and/or fever due to infections, changing PH levels due to certain bacteria infections and increased moisture due to discharge from bacteria growth. Would enable a caretaker to avoid changing bandages when not needed, causing unnecessary need for new infections by breaking the scab seal protecting the development of new skin.

In other embodiments the temperature sensor can be combined with sensors like audio, noise, sound, and an accelerometer as this would serve as a e.g. snoring and apnea detector, combining audio and vibration to provide low cost tests for the home health care market.

In yet other embodiments a combination of sensors like temperature, accelerometer, displacement and force would e.g. provide means of detecting joint flexibility and use after a e.g. knee meniscus surgery, and even detecting local temperature development caused by infection or inflammation in the knee. Providing the patient and doctor information to improve care and restitution.

In yet other embodiments images is captured of the patient's fever rash, blushing, skin colour. This is used together with temperature patterns and other vital data gathered from the patient to monitor patient. Temporal development of the rash can be used to determine illness together with fever pattern.

INDUSTRIAL APPLICABILITY

The invention according to the application finds use in continuous monitoring of core temperature of an organism. Examples of which can be monitoring of livestock for illness and fertility to maximize production and yield, through reduced illness and improved timing for insemination.

The invention claimed is:
1. A sensor for measuring a temperature of an organism, comprising:
 a first layer configured to be in thermal contact with a surface of an organism;
 a second layer of an insulating material in contact with and on top of the first layer;
 a first temperature sensor in thermal connection with the first layer via a thermal conductor through the second layer; and a second temperature sensor configured to be thermally insulated from an organism, the first and second temperature sensors being located above the second layer;

the sensor further comprising a radiating element, wherein the first layer is a reflector for the radiating element, and the insulating material creates a distance between an antenna, the radiating element and the reflector; and wherein the radiating element, the insulating material, and the reflector form an energy storage unit for storing harvested electrical energy.

2. The sensor according to claim 1, further comprising a third layer connected to and above the second layer, wherein the third and the first layer comprise a metallic material.

3. The sensor according to claim 2, further comprising a device for harvesting electrical energy, wherein the harvested energy is stored in the energy storage unit.

4. The sensor according to claim 3, wherein the energy storage unit is at least one capacitive storage formed of at least two metallic layers and at least one insulating layer of the sensor.

5. The sensor according to claim 4, wherein the reflector comprises a capacitive storage device for storing harvested energy from the energy harvesting device.

6. The sensor according to claim 3, further comprising a processing unit for sampling the first and second temperature sensors.

7. The sensor according to claim 3, wherein the reflector comprises a capacitive storage device for storing harvested energy from the energy harvesting device.

8. The sensor according to claim 3, wherein the radiating element functions as a receiving element for energy harvesting.

9. The sensor according to claim 2, further comprising a processing unit for sampling the first and second temperature sensors.

10. The sensor according to claim 2, wherein the radiating element functions as a receiving element for energy harvesting.

11. The sensor according to claim 1, further comprising a processing unit for sampling the first and second temperature sensors.

12. The sensor according to claim 11, wherein the energy storage unit is at least one capacitive storage formed of at least two metallic layers and at least one insulating layer of the sensor.

13. The sensor according to claim 11, wherein the reflector comprises a capacitive storage device for storing harvested energy from the energy harvesting device.

14. The sensor according to claim 1, wherein the radiating element is configured to function as a receiving element for energy harvesting.

15. The sensor according to claim 1, wherein a processing unit is coupled to at least one selected from the group comprising an energy harvesting device, energy storage unit, and a capacitive storage device for powering the processing unit to sample data from at least one sensor, and the processing unit is coupled to the radiating element for transmission of at least one sampled sensor data.

16. The sensor according to claim 15, wherein the sensor further comprises an indicator coupled to the processing unit.

17. A method for estimating a core temperature of an organism using a sensor according to claim 1 placed on a surface of an organism, wherein the method comprises:

measuring a temperature from the first temperature sensor, measuring a temperature from the second temperature sensor, and calculating a core temperature according to heat flux calculations using the measurement from the first and the second temperature sensors.

18. A sensor for measuring a temperature of an organism comprising:

a first layer configured to be in thermal contact with a surface of an organism;

a second layer of an insulating material in contact with and on top of the first layer;

a first temperature sensor in thermal connection with the first layer via a thermal conductor through the second layer; and a second temperature sensor configured to be thermally insulated from an organism, the first and second temperature sensors being located above the second layer;

the sensor further comprising a radiating element, wherein the first layer is a reflector for the radiating element, and the insulating material creates a distance between an antenna, the radiating element and the reflector;

wherein the radiating element, the insulating material, and the reflector form an energy storage unit for storing harvested electrical energy; and wherein the reflector comprises a capacitive storage device for storing harvested energy from the energy harvesting device.

19. The sensor for measuring temperature of an organism comprising:

a first layer configured to be in thermal contact with a surface of an organism;

a second layer of an insulating material in contact with and on top of the first layer;

a first temperature sensor in thermal connection with the first layer via a thermal conductor through the second layer; and a second temperature sensor configured to be thermally insulated from an organism, the first and second temperature sensors being located above the second layer;

the sensor further comprising a radiating element, wherein the first layer is a reflector for the radiating element, and the insulating material creates a distance between an antenna, the radiating element and the reflector;

wherein the radiating element, the insulating material, and the reflector form an energy storage unit for storing harvested electrical energy;

a third layer connected to and above the second layer, wherein the third and the first layer comprise a metallic material; and wherein the reflector comprises a capacitive storage device for storing harvested energy from the energy harvesting device.

* * * * *